(12) United States Patent
Yoder

(10) Patent No.: US 10,993,459 B2
(45) Date of Patent: May 4, 2021

(54) METHOD FOR UNLOCKING BIOACTIVE PROTEINS

(71) Applicant: Ralph Yoder, Ames, IA (US)

(72) Inventor: Ralph Yoder, Ames, IA (US)

( * ) Notice: Subject to any disclaimer, the term of this patent is extended or adjusted under 35 U.S.C. 154(b) by 0 days.

(21) Appl. No.: 16/819,290

(22) Filed: Mar. 16, 2020

(65) Prior Publication Data

US 2021/0084932 A1    Mar. 25, 2021

Related U.S. Application Data

(60) Provisional application No. 62/904,208, filed on Sep. 23, 2019.

(51) Int. Cl.
| | | |
|---|---|---|
| *A23J 1/20* | (2006.01) | |
| *A23J 3/34* | (2006.01) | |
| *A23L 33/16* | (2016.01) | |
| *C07K 1/107* | (2006.01) | |

(52) U.S. Cl.
CPC ............... *A23J 3/343* (2013.01); *A23L 33/16* (2016.08); *C07K 1/107* (2013.01)

(58) Field of Classification Search
None
See application file for complete search history.

(56) References Cited

U.S. PATENT DOCUMENTS

| | | | |
|---|---|---|---|
| 4,436,658 A | * | 3/1984 | Peyrouset ............... A23J 1/205 |
| | | | 530/387.1 |
| 8,389,039 B2 | | 3/2013 | Wu et al. |
| 9,416,156 B2 | | 8/2016 | Home et al. |
| 2004/0219224 A1 | | 11/2004 | Yakovlevsky et al. |
| 2012/0058195 A1 | | 3/2012 | Harel |
| 2014/0093912 A1 | | 4/2014 | Hussain et al. |
| 2014/0295521 A1 | | 10/2014 | Herne |

* cited by examiner

*Primary Examiner* — Robert T. Crow
*Assistant Examiner* — John P Nguyen
(74) *Attorney, Agent, or Firm* — Boudwin Intellectual Property; Daniel Boudwin

(57) ABSTRACT

A method for unlocking bioactive proteins that can then be used to activate natural remedies. The method includes starting with Silica salt and water mixture. Then a base of whey protein concentrate is added to the mixture. The pH of the whey protein mixture is raised using a base. The pH is held at a level above 11 for at least two hours. After at least two hours an acid is then added to the mixture to bring the pH of the mixture below 3 pH. This will stop the activation process. After the unattached proteins are removed the protein mixture is then brought back to a normal pH level, around 4 pH.

9 Claims, 2 Drawing Sheets

METHOD FOR UNLOCKING BIOACTIVE PROTEINS

CROSS REFERENCE TO RELATED APPLICATIONS

This application claims the benefit of U.S. Provisional Application No. 62/904,208 filed on Sep. 23, 2019. The above identified patent application is herein incorporated by reference in its entirety to provide continuity of disclosure.

BACKGROUND OF THE INVENTION

The present invention relates to a method for unlocking bioactive proteins. More particularly, the present invention provides a method for creating bioactive proteins that can then be used for natural remedies.

The innate immune system of man and animals is easily the most effective biological system to maintain health. It is more effective than any medicine. It rapidly identifies, destroys and returns the body back to a normal state. This occurs from birth until death. The bio-active proteins from whey when separated, activated and applied correctly acts to activate the innate immune system resulting in the body returning to normal rapidly after an injury or illness. The net result is a lower morbidity rate and significantly less expense related to diagnosis and treatment of many health events throughout life. Since similar proteins are introduced to the body at birth and in the early stages of life it would seem most practical that it should be used on a regular basis as the first response to essentially all health issues that come up in life.

The bioactive protein has two distinct modes of action. The first when the bio-active fraction is taken orally the epithelial cells have known receptors that almost immediately start a series of bio-chemical reactions. There are a significant number of these receptor cells in the oral and respiratory cavity. Bioactive proteins very clearly act biochemically and very rapidly based on several observations and backed by solid research data where buccal epithelial cells were activated when treated by colostrum. These reactions cause signals to go very rapidly to the areas that are being challenged and very rapidly carry out multiple functions that are needed to stop the infection or challenge.

The second mode of action is through colostrum. Colostrum is a form of mother's milk that is produced in an infant's first weeks of life. Colostrum provides nutrients in which proteins are broken down and absorbed more effectively. Colostrum further has antibodies that help to quickly boost an infant's immune system. This helps to ensure that the infant does not catch illnesses due to their new weak immune systems. Currently, these effects of colostrum are lost after the initial stages of life.

For example, in calves and pigs there is almost no blood transfer in the womb from mother to youngling. This means that the immunity of the newborn animals is very weak in these animals at birth. If young animals do not receive colostrum they will likely die. This means that if animal's mother does not produce milk or if the mother dies at birth the young animal has a high death rate as well.

Consequently, there is a need for an improvement in the art of creating natural remedies for health issues and unlocking proteins found in colostrum. The present invention substantially diverges in design elements from the known art while at the same time solves a problem many people face when looking for natural remedies for health issues and continuing the advantages from proteins by transforming them into a different biological make-up. In this regard the present invention substantially fulfills these needs.

SUMMARY OF THE INVENTION

The present invention provides a method for unlocking bioactive proteins by manipulating the pH of the protein, wherein the same can be utilized for providing convenience for the user when looking for alternative medicines. The method for unlocking bioactive proteins comprises, creating a mixture comprising of water, silica salt, whey protein. In one embodiment the mixture further includes at least one percent of plasma protein by mass. Adding a base to the mixture raising the pH level above 11 pH. Adding an acid to the mixture lowering the pH level below 3 pH. Adding another base to the protein mixture to raise the pH level above 4 pH. Maintaining the pH balance between 4 pH and 5 pH.

Another object of the method for unlocking bioactive proteins is to raise the pH level to between 11 pH and 12 pH.

Another object of the method for unlocking bioactive proteins is to use an amount of silica salt that is between 3 and 8 percent of the total dry matter.

Yet another object of the method for unlocking bioactive proteins is to use an amount of silica salt equal to five percent of the total mass of the protein mixture.

Another object of the method for unlocking bioactive proteins is to reduce the pH to between 2 pH and 2.5 pH.

Another object of the method for unlocking bioactive proteins is to rise the pH level the first time for at least two hours.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
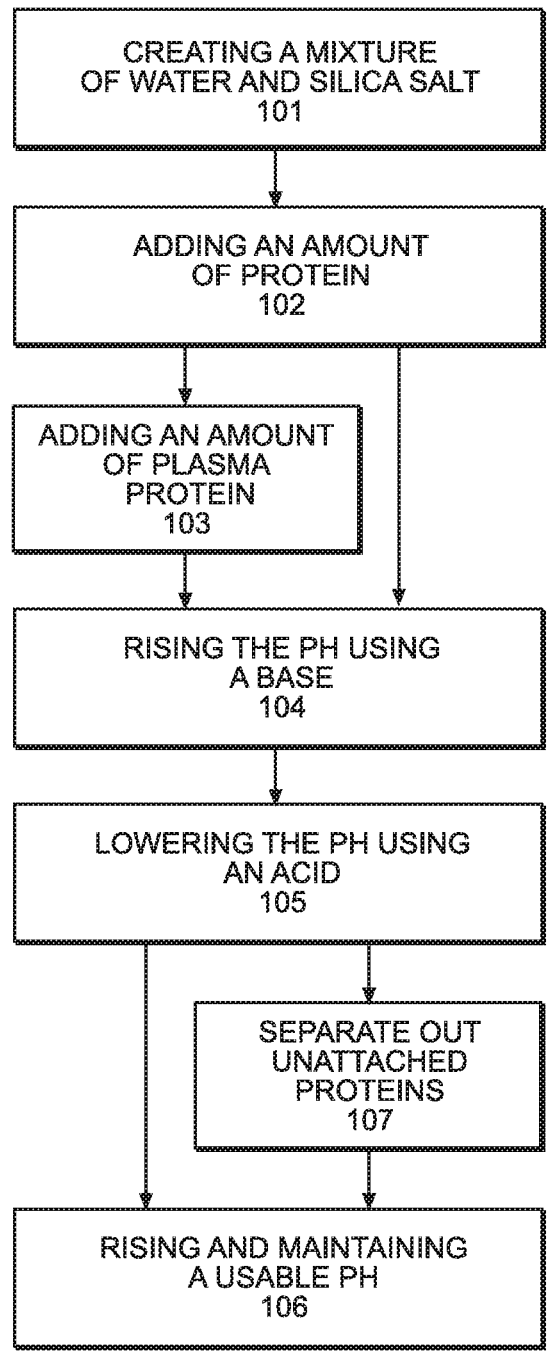
FIG. 1 shows a flow chart of an embodiment of the method for activating bioactive proteins.

Reference is made herein to the attached drawings. Like reference numerals are used throughout the drawings to depict like or similar elements of the method for activating bioactive proteins. For the purposes of presenting a brief and clear description of the present invention, a preferred embodiment will be discussed as used for the method for activating bioactive proteins. The figures are intended for representative purposes only and should not be considered to be limiting in any respect.

Referring now to FIG. 1, there is shown a flow chart of an embodiment of the method for activating bioactive proteins. The method starts by creating mixture of water and silica salt 101. The amount of silica salt is between three percent of the dry matter weight and eight percent of the dry matter weight. In one embodiment the percentage is five percent of silica salt by dry matter weight. In one embodiment Nalco is the silica salt product used. The silica salt allows the unlocked proteins to adhere to the substance, thus separating the smaller protein bands.

Next, an amount of protein is added to the mixture 102. In one embodiment the protein is one hundred percent whey protein. In one embodiment the starting protein is a dry protein. In another embodiment the starting protein is a procream or wet protein. In another embodiment the mixture has a percentage of plasma protein added to the whey protein 103. In one of these embodiments the plasma protein makes up between 1 percent to 5 percent of the volume by mass.

Next the desired mixture will have the pH level risen 104. The base product should be added as needed until the pH reaches a level above 11 pH. In one embodiment the pH level is balanced at a level between 11 pH and 13 pH. The pH is raised by titrating the mixture using a base product. In one embodiment the pH level is risen for at least two hours. In other embodiments the pH balance is raised for more than two hours. In some embodiments there needs to be a constant stirring when adding the base product. This will ensure that the protein is properly mixed and the pH stays at the appropriate levels. The rising of the pH in this range will cause the proteins to disperse into smaller protein bands. At this time this keeps the proteins unlocked in the new form.

After the desired time has been reached the pH is then brought down to a low level using an acid 105. In one embodiment the pH is reduced to between two pH and three pH. In one embodiment the pH level is lowered to two and a half pH. In one embodiment a hydrochloric acid is used. This lowering of the pH will stop the unlocking process and prevent the protein mixture from degrading. When the pH is lowered by adding acid to the mixture the carrier protein in the whey is released and these proteins cling together and can be separated from the liquid in the mixture.

In one embodiment the mixture will then be separated 107. This sorting will remove the liquid and unattached protein from the new unlocked and attached proteins. In one embodiment a centrifuge may be used to sort the mixture. The centrifuge will allow the useable product to be separated from the product that has not been changed. Further, the centrifuge will sort product into a product that can be finished then used.

Once the process has been halted the protein mixture must be brought back to a useable pH level. Another base is added to the mixture 106. The pH level is brought up to a level between three pH and five pH. This level will allow the proteins to be used in a wide variety of products. Finally, the mixture is cleaned 106.

Figure 2:
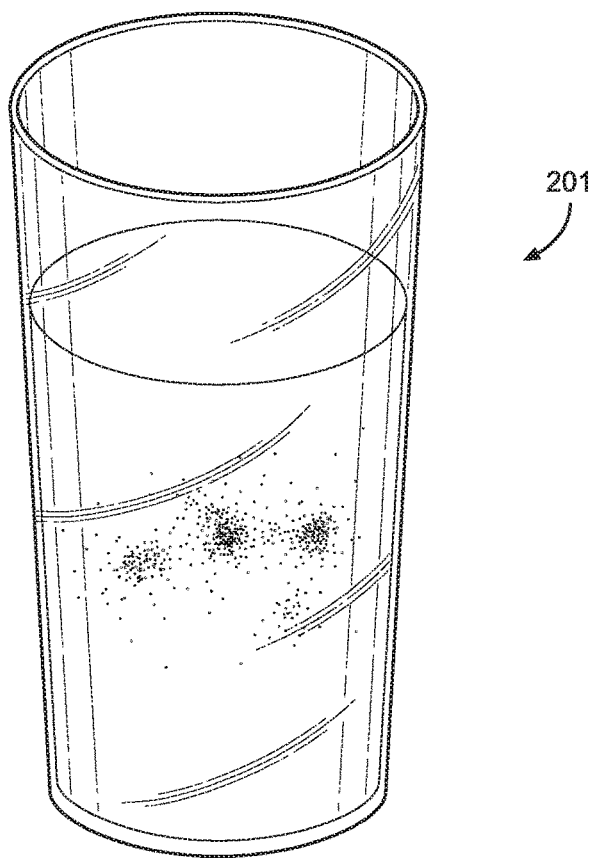
FIG. 2 shows a perspective view of an embodiment of a product made using bio active protein.

Referring now to FIG. 2, there is shown a perspective view of an embodiment of a product made using bio active protein. Once the proteins have been unlocked many different products can be made. In one embodiment the proteins may be taken orally. In this embodiment the proteins may be turned into a drink 201.

Figure 3:
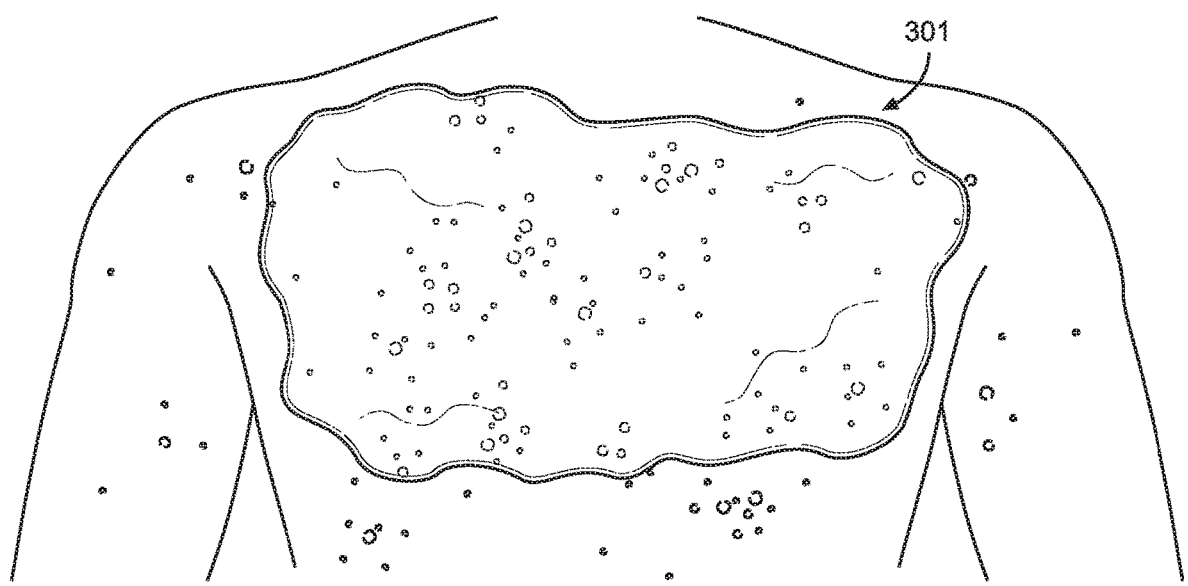
FIG. 3 shows a perspective view of another embodiment of a product made using bio active protein.

Referring now to FIG. 3, there is shown a perspective view of another embodiment of a product made using bio active protein. In another embodiment a salve 301 can be made using the unlocked protein.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of making unlocked bioactive proteins comprising:
    creating a mixture composed of water, silica salt, and a combination of one or more base proteins selected from the group of: whey protein, dry protein, wet protein, and plasma protein;
    titrating the mixture with a base until the mixture comprises a first pH level greater than 11;
    maintaining the first pH level for a threshold amount of time;
    adding an acid to the mixture until the mixture comprises a second pH level less than 3;
    adding a base to the mixture until the mixture comprises a third pH level between 3 and 5.

2. The method of claim 1, wherein the mixture comprises silica salt in an amount between 3% and 8% of a dry matter weight of the mixture.

3. The method of claim 1, wherein the mixture comprises plasma proteins in an amount between 1% and 5% of a volume of the mixture.

4. The method of claim 1, wherein the threshold amount of time is greater than or equal to two hours.

5. The method of claim 1, further comprising:
    stirring the mixture during the entire duration of the titrating step.

6. The method of claim 1, wherein the acid comprises hydrochloric acid.

7. The method of claim 1, further comprising:
    sorting the mixture to separate attached proteins from unattached proteins.

8. The method of claim 7, wherein the sorting step is accomplished via a centrifuge.

9. The method of claim 7, further comprising:
    removing the unattached proteins from the mixture after the mixture reaches the third pH level.

* * * * *